US010711049B2

(12) United States Patent
Lee et al.

(10) Patent No.: US 10,711,049 B2
(45) Date of Patent: Jul. 14, 2020

(54) METHOD FOR PRODUCING TLR5 AGONIST PROTEIN

(71) Applicant: KOREA INSTITUTE OF INDUSTRIAL TECHNOLOGY, Cheonan-si, Chungcheongnam-do (KR)

(72) Inventors: Woo-Jong Lee, Seongnam-si (KR); Sung-Gun Kim, Chungcheongbuk-do (KR); Dong-Mok Lee, Daegu (KR); Hee-Kyung An, Daegu (KR); Chi-Min Choi, Seongnam-si (KR)

(73) Assignee: Korea Institute of Industrial Technology, Cheonan-si, Chungcheongnam-do (KR)

(*) Notice: Subject to any disclaimer, the term of this patent is extended or adjusted under 35 U.S.C. 154(b) by 5 days.

(21) Appl. No.: 15/553,191

(22) PCT Filed: Jun. 21, 2016

(86) PCT No.: PCT/KR2016/006581
§ 371 (c)(1),
(2) Date: Aug. 24, 2017

(87) PCT Pub. No.: WO2016/208942
PCT Pub. Date: Dec. 29, 2016

(65) Prior Publication Data
US 2019/0127434 A1 May 2, 2019

(30) Foreign Application Priority Data
Jun. 23, 2015 (KR) .......................... 10-2015-0089284

(51) Int. Cl.
C07K 14/47 (2006.01)
C07K 14/705 (2006.01)
C07K 19/00 (2006.01)
C12N 15/63 (2006.01)
G01N 33/53 (2006.01)
G01N 33/538 (2006.01)
C12N 15/62 (2006.01)

(52) U.S. Cl.
CPC ............ C07K 14/705 (2013.01); C07K 14/47 (2013.01); C07K 19/00 (2013.01); C12N 15/62 (2013.01); C12N 15/63 (2013.01); G01N 33/53 (2013.01); G01N 33/538 (2013.01); C07K 2319/00 (2013.01); C07K 2319/20 (2013.01); C07K 2319/21 (2013.01); C07K 2319/50 (2013.01); C07K 2319/75 (2013.01); C07K 2319/95 (2013.01)

(58) Field of Classification Search
CPC .... C07K 14/255; C07K 14/195; C07K 19/00; A61K 35/68; C12N 15/09; C12N 15/63
See application file for complete search history.

(56) References Cited

U.S. PATENT DOCUMENTS

| 7,771,970 | B2* | 8/2010 | Lee ................ C07K 14/00 435/69.7 |
| 8,007,812 | B2* | 8/2011 | Gudkov .............. A61K 38/164 424/190.1 |
| 8,236,327 | B2 | 8/2012 | Rhee et al. |
| 8,337,864 | B2 | 12/2012 | Rhee et al. |
| 8,337,865 | B2 | 12/2012 | Rhee et al. |
| 2011/0135596 | A1 | 6/2011 | Lee et al. |
| 2014/0045211 | A1* | 2/2014 | Handel .............. C07K 14/521 435/68.1 |

FOREIGN PATENT DOCUMENTS

| JP | 2005-506319 A | 3/2005 |
| JP | 2008-525472 A | 7/2008 |
| KR | 10-2008-0074556 A | 8/2008 |
| KR | 10-2009-0085433 A | 8/2009 |
| KR | 10-2011-0062997 A | 6/2011 |
| KR | 10-2012-0104177 A | 9/2012 |
| KR | 10-1287905 B1 | 7/2013 |
| WO | WO-2015/080631 A1 | 6/2015 |

OTHER PUBLICATIONS

Baker et al. Protein expression using ubiquitin fusion and cleavage. Curr Opin Biotechnol 7: 541-546, 1996.*
Burdelya et al. An agonist of toll-like receptor 5 has radioprotective activity in mouse and primate models. Science 320: 226-230, 2008 (includes Supplement).*
Finley et al. The tails of ubiquitin precursors are ribosomal proteins whose fusion to ubiquitin facilitates ribosome biogenesis. Nature 338: 394-401, 1989.*
Gilchrist et al. A ubiquitin-specific protease that efficiently cleaves the ubiquitin-proline bond. J Biol Chem 272(51): 32280-32285, 1997.*
Kim et al. Radioprotective effect of newly synthesized toll-like receptor 5 agonist, KMRC011, in mice exposed to total-body irradiation. J Radiation Res 60(4): 432-441, 2019.*
Lodish et al., Molecular Cell Biology. 4th edition. New YorK: W.H. Freeman; 2000. Section 9.1, Molecular Definition of a Gene.*
Song et al. TLR5 binding and activation by KMRC011, a flagellin-derived radiation countermeasure. Biochem Biophys Res Comm 508: 570-575, 2019.*
Definition of "gene" from Merriam-Webster Dictionary, www.merriam-webster.com/dictionary/gene; accessed Sep. 4, 2019.*
Catanzariti et al. An efficient system for high-level expression and easy purification of authentic recombinant proteins. Protein Sci 13: 1331-1339, 2004.*

(Continued)

Primary Examiner — Bridget E Bunner
(74) Attorney, Agent, or Firm — Rabin & Berdo, P.C.

(57) ABSTRACT

The present disclosure relates to a method for producing a TLR5 agonist protein. According to the present disclosure, the TLR5 agonist protein can be easily separated and purified after biotechnological production. In particular, the fusion partner used for separation and purification is effectively removed so as to minimize the possibility of inhibiting binding to TLR5 and inducing an immune response by the fusion partner.

10 Claims, 6 Drawing Sheets
Specification includes a Sequence Listing.

(56) References Cited

OTHER PUBLICATIONS

Pilon et al. Ubiquitin fusion technology: bioprocessing of peptides. Biotechnol Prog 13: 374-379, 1997.*

Varshaysky, A. Ubiquitin fusion technique and related methods. Methods Enzymol 399: 777-799, 2005.*

Xu et al. High-level expression of the recombinant hybrid peptide cecropinA(1-8)-magainin2(1-12) with an ubiquitin fusion partner in *Escherichia coli*. Protein Exp Purification 55: 175-182, 2007.*

Keiji Wada et al., "Deubiquitinating enzymes", 医学のあゆみ, vol. 211, Issue 1, 23-28 (2004).

Japanese Office Action dated Aug. 20, 2018.

Fabien Loison et al., "A Ubiquitin-Based Assay for the Cytosolic Uptake of Protein Transduction Domains", Molecular Therapy, vol. 11, No. 2, pp. 205-214, Feb. 2005.

Japanese Office Action dated Aug. 20, 2018, in application 2017-542423.

* cited by examiner

FIG.1

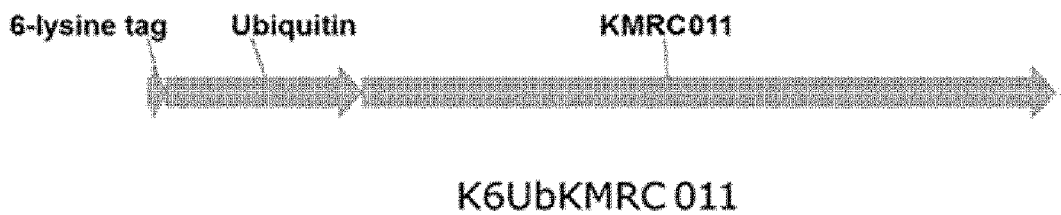

K6UbKMRC011

FIG. 2 atgaagaaaaaaaagaaaaagcagattttcgtcaagactttgaccggtaaaaccataacattggaagttg
aatcttccgataccatcgacaacgttaagtcgaaaattcaagacaaggaaggtatccctccagatcaaca
aagattgatctttgccggtaagcagctagaagacggtagaacgctgtctgattacaacattcagaaggag
tccaccttacatcttgtgctaaggctaagaggtggcgcgcaggttatcaacaccaactctctgtccctgct
gacccaaaacaatctgaacaaatcccagagctccctgagctccgcgatcgagcgtctgtcctccggcct
gcgtattaatagcgccaaagacgatgccgcgggtcaggcgatcgctaaccgcttcacttccaacattaa
aggcctgactcaggcctcccgtaacgcaaacgacggtattagcatcgctcagactactgaaggtgctct
gaacgaaattaacaacaacctgcagcgcgtccgtgaactgagcgtccaggcaaccaacggtactaactc
tgacagcgatctgaaatccattcaggatgaaattcagcagcgtctggaagaaatcgaccgcgtgtctaac
cagacgcaattcaacggcgtaaaggtgctgtctcaggacaatcagatgaaaatccaagttggtgcgaac
gacggcgagactatcaccatcgatctgcagaaaatcgacgttaaatccctgggtctggacggttttaacg
taaactctccaggtatctctggtggcggtggtggcattctggactccatgggtacctgatcaacgagga
tgcagcggcggctaagaaatctactgccaaccctctggccagcatcgacagcgctctgagcaaagttga
tgcggtgcgttcttctctgggcgcaatccagaatcgcttcgattccgctatcacgaatctgggcaacacc
gttaccaacctgaactctgctcgtagccgtatcgaagacgcagattatgcgaccgaagtatctaacatgt
ctaaagcacagattctgcagcaggctggtacctctgttctggctcaggcaaccaggtgccgcaaaacg
ttctgtctctgctgcgctaa (SEQ ID NO: 7)

* Base sequence corresponding to K6Ub is underlined.
* Base sequence of the linker is shown in bold and underlined.

FIG. 3

MKKKKKKQIFVKTLTGKTITLEVESSDTIDNVKSKIQDKEGIPPDQQRLIFAGKQLEDGR
TLSDYNIQKESTLHLVLRLRGGAQVINTNSLSLLTQNNLNKSQSSLSSAIERLSSGLRINS
AKDDAAGQAIANRFTSNIKGLTQASRNANDGISIAQTTEGALNEINNNLQRVRELSVQAT
NGTNSDSDLKSIQDEIQQRLEEIDRVSNQTQFNGVKVLSQDNQMKIQVGANDGETITIDLQ
KIDVKSLGLDGFNVNSPGISGGGGGILDSMGTLINEDAAAAKKSTANPLASIDSALSKVD
AVRSSLGAIQNRFDSAITNLGNTVTNLNSARSRIEDADYATEVSNMSKAQILQQAGTSVL
AQANQVPQNVLSLLR (SEQ ID NO: 8)

* Amino acid sequence corresponding to K6Ub is underlined.
* Amino acid sequence of the linker is shown in bold and underlined.

FIG. 4

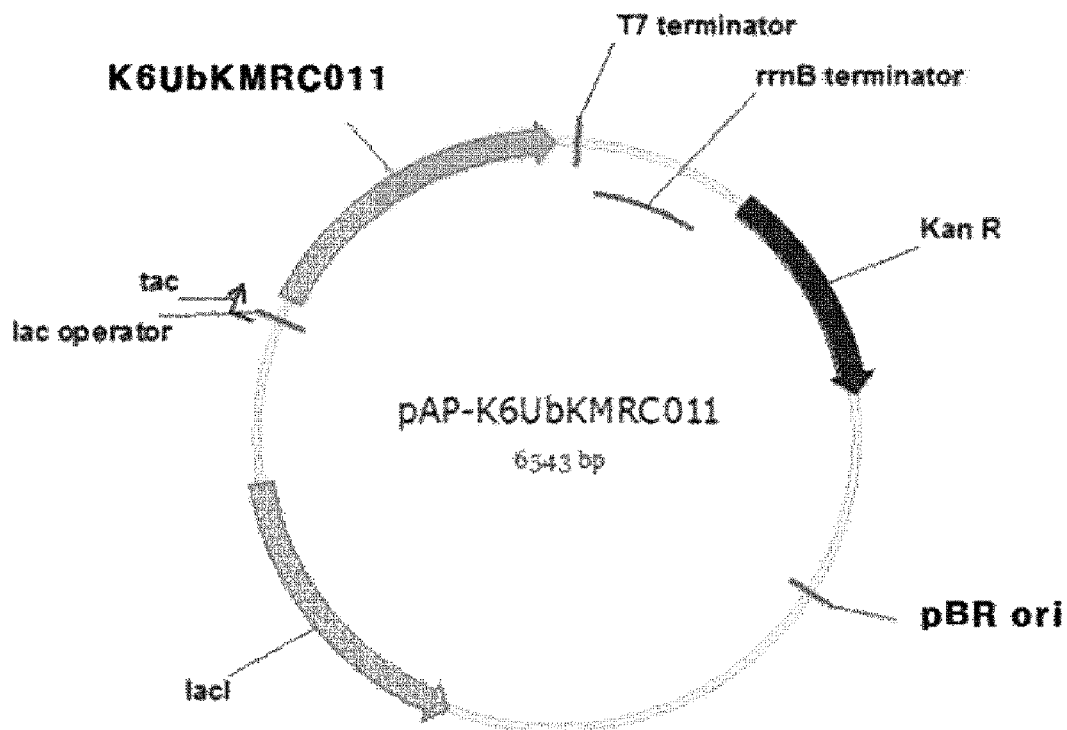

M, marker protein; T, total cellular protein; S, soluble protein fraction;
I, insoluble protein fraction; BI, cell before induction; AI: cell after induction Arrow indicates location of expressed K6UbKMRC011

M, marker protein, IB, solubilized inclusion body protein,
FT, protein fraction not binding to cation exchange resin; E1 – E5, elution fraction Arrow indicates location of expressed K6UbKMRC011

M, marker protein; C, K6UbKMRC011 without USP1 treatment,
U, K6UbKMRC011 with USP1 treatment M, marker protein; O, TLR5 agonist obtained by on-column cleavage (KMRC011)

METHOD FOR PRODUCING TLR5 AGONIST PROTEIN

SEQUENCE LISTING SPECIFIC REFERENCE

This application contains a Sequence Listing submitted via EFS-Web and hereby incorporated by reference in its entirety. The Sequence Listing is named MIP-330NP-KITECH_ST25.txt, created on Oct. 4, 2018 and revised on Nov. 4, 2019, and 9.18 kilobytes in size.

TECHNICAL FIELD

The present disclosure relates to a method for producing a TLR5 agonist protein, and more particularly, to a method for producing a TLR5 agonist protein which can be easily separated and purified after being produced through a biological process, and in which a fusion partner can be furtherly effectively removed.

BACKGROUND ART

Entolimod is a remedy for radiation exposure, which was developed by Cleveland Biolabs under the support of the United States Department of Defense, and the present disclosure is to produce the "improved entolimod (KMRC011)" as a TLR5 agonist, in which the pre-developed entolimod has been partially modified.

The entolimod was derived from the flagellin protein of *Salmonella enterica*. It is found that the emtoilimod blocks cell death due to radiation exposure through binding and activation with TLR5 (Toll-like receptor-5). There is a report that in fact, approximately 67% was survived after exposure to monkeys with radiation levels similar to those exposed to firefighters participated at the Chernobyl nuclear accident site, and the entolimod was administrated to the monkeys. On the other hand, the survival rate of monkeys without the substance was approximately 25%.

The entolimod consists of the D0 domain and the D1 domain that directly bind to TLR5 among the flagellin proteins of *Salmonella enterica* composed of a total of four domains (D0, D1, D2, and D3). The amino terminal thereof includes 34 amino acid residues (MRGSHHHHHHGMASMTGGQQMGRDLYDDDDKDPM (SEQ ID NO: 9)) including the 6-histidine tag and the enterokinase recognition sequence for the purification and the cleavage.

However, the conventional entolimod needs to be removed because it is likely to inhibit binding to TLR5 and induce an immune response by the 34 amino acid residues bound to the amino terminal.

However, since the internal amino acid sequence of the entolimod has a structure vulnerable to protease, there may be a problem that the structure may be destroyed when it is treated with the enterokinase, a kind of protease.

Therefore, a new concept of the entolimod and a method for preparation thereof needs to be developed.

Meanwhile, Korean Patent No. 10-1287905 (issued on Jul. 15, 2013) discloses a method for protecting a patient from radiation using a flagellin, and a method for protecting a patient from one or more treatments inducing apoptosis, which includes administering a composition including a pharmaceutically acceptable amount of the reagent inducing NF-kB to a patient.

Further, Korean Patent Publication No. 10-2012-0104177 (published on Sep. 20, 2012) discloses methods and medicaments for treating cancers and infectious diseases by providing TLR5 for treating cancer and TLR5 agonist such as a flagellin as an agonist.

DISCLOSURE

Technical Problem

The present disclosure has been made to address the above-mentioned issues and is to provide a method for providing a TLR5 agonist protein minimizing the possibility of inhibition of binding with TLR5 and induction of the immune response due to a fusion partner by effectively removing the fusion partner used for separation and purification.

Technical Solution

The present disclosure relates to a fusion protein characterized in that ubiquitin is bound to a TLR5 agonist protein formed by combining a polypeptide having an amino acid sequence as set forth in SEQ ID NO: 2 with a polypeptide having an amino acid sequence as set forth in SEQ ID NO: 4.

The TLR5 agonist of the present disclosure specifically binds to TLR5, a receptor of the cell, and activates intracellular innate immunity, thereby controlling cell damage caused by radiation exposure.

To produce the TLR5 agonist protein by bioprocessing with use of microorganisms, consideration should be given to the separation and purification of the 'produced TLR5 agonist protein.' Due to such need, Cleveland Biolabs company produced the entolimod by adding 34 amino acid residues (MRGSHHHHHHGMASMTGGQQMGRDLYDDDDKDPM (SEQ ID NO: 9)) including the 6-histidine tag and the enterokinase recognition sequence for the purification and the cleavage to the D0 domain and the D1 domain, which directly bind to TLR5, among flagellin proteins of *Salmonella enterica*.

However, the above 34 amino acid sequences bound to the fusion partner are preferably removed because of the possibility of induction of the immune response and inhibition of binding with TLR5. Since the D0 domain and the D1 domain are structurally vulnerable to protease, thus, despite the presence of the enterokinase recognition sequence, it is used while the fusion partner (34 amino acid sequences) is not removed by the treatment thereof.

The present disclosure aims to solve such a problem. The ubiquitin used as the fusion partner in the present disclosure may be cleaved by a ubiquitin cleavage enzyme (for example, ubiquitin-specific protease (USP) or ubiquitin C-terminal hydrolase (UCH)). The ubiquitin cleavage enzyme has a very high substrate specificity and has the advantage of selectively cleaving only the site to which the ubiquitin is bound without cleaving other sites in the protein (entolimod). The present disclosure produces the TLR5 agonist protein (hereinafter also referred to as an 'improved entolimod') in which the fusion partner is clearly removed using the above-mentioned characteristic of ubiquitin, thereby completing the present disclosure.

The ubiquitin is a protein known as an expression derivative that assists in the expression of a target protein and can be cleaved and removed by the ubiquitin cleavage enzymes (for example, USP or UCH) during the purification process. In the present disclosure, the ubiquitin may use only some sequences in addition to the entire sequences.

In the fusion protein of the present disclosure, the TLR5 agonist protein may be, for example, a combination of a polypeptide having an amino acid sequence as set forth in SEQ ID NO: 2 and a polypeptide having an amino acid sequence as set forth in SEQ ID NO: 4 via a linker as set forth in SEQ ID NO: 6. The polypeptide as set forth in SEQ ID NO: 2 and the polypeptide as set forth in SEQ ID NO: 4 are folded by their binding to form a D0 domain and a D1 domain that can directly bind to TLR5. In this case, the polypeptide as set forth in SEQ ID NO: 2 and the polypeptide as set forth in SEQ ID NO: 4 can be coupled by a linker, which may be, for example, a polypeptide of the amino acid sequence as set forth in SEQ ID NO: 6.

In the fusion protein of the present disclosure, the ubiquitin is preferably fused to the amino terminal of the TLR5 agonist protein.

In the fusion protein of the present disclosure, the ubiquitin preferably includes an amino acid sequence which is cleaved by the ubiquitin cleavage enzyme. If the ubiquitin includes the amino acid sequence cleaved by the ubiquitin cleavage enzyme, even a part of the ubiquitin, not entire ubiquitin, may be used in the present disclosure.

In the fusion protein of the present disclosure, the ubiquitin cleavage enzyme may be various ones, for example, USP and UCH.

In the fusion protein of the present disclosure, further, the fusion protein preferably has a tag for purification attached to the amino terminal of the ubiquitin. However, when the tag for purification is bound, it has an advantage of facilitating separation and purification. At this time, the tag for purification may be various tags known in the art. For example, a lysine tag formed by six consecutive bonds of lysines or a histidine tag (His-tag) can be used.

Meanwhile, the present disclosure provides a method for producing a TLR agonist protein, including the steps of: (a) producing a vector including a fusion gene in which a gene encoding the TLR agonist protein formed in a combination of a polypeptide having the amino acid sequence as set forth in SEQ ID NO: 2 and a polypeptide having the amino acid sequence as set forth in SEQ ID NO: 4, binds to a gene encoding the ubiquitin binding to a gene encoding a tag for purification; (b) producing a fusion protein by transforming a host with the vector prepared above and then expressing the fusion gene; (c) recovering the fusion protein by binding the above-produced fusion protein to a column to which the tag for purification, which is fused in the fusion protein, binds; and (d) recovering the TLR5 agonist protein by treating the above-recovered fusion protein with a ubiquitin cleavage enzyme to cleave the site to which the ubiquitin binds. Hereinafter, each of the above-described steps will be described in more detail.

Step (a): Production of Vector Containing Fusion Gene

The present step is to produce the vector including the fusion gene in which the gene encoding the TLR agonist protein formed in the combination of the polypeptide having the amino acid sequence as set forth in SEQ ID NO: 2 and the polypeptide having the amino acid sequence as set forth in SEQ ID NO: 4, binds to the gene encoding the ubiquitin binding to the gene encoding the tag for purification. Binding of genes and production of vectors can be performed using techniques well known in the art, so detailed description thereof will be omitted.

In the present step, the TLR5 agonist protein is, for example, the combination of the polypeptide having the amino acid sequence as set forth in SEQ ID NO: 2 and the polypeptide having the amino acid sequence as set forth in SEQ ID NO: 4 via the linker as set forth in SEQ ID NO: 6.

In the present step, the gene encoding the ubiquitin preferably binds to 5' terminal of the gene encoding the TLR5 agonist protein, and the gene encoding the tag for purification preferably binds to 5' terminal of the gene encoding the ubiquitin.

In the present step, the fusion gene may, for example, be one having the nucleic acid sequence as set forth in SEQ ID NO: 7.

In the present step, the ubiquitin preferably contains an amino acid sequence that is cleaved by the ubiquitin cleavage enzyme. However, a portion of the ubiquitin may also be used if it contains the amino acid sequence cleaved by the ubiquitin cleavage enzyme.

In the present step, the tag for purification may use various tags for purification, and for example, a lysine tag formed by six consecutive bonds of lysines or a histidine tag (His-tag) can be used.

Step (b): Production of Fusion Protein

The present step is to produce the fusion protein by transforming the host with the above-prepared vector and expressing the fusion gene.

In present step, the host may be a host that can introduce the vector constructed in the previous step and express the gene introduced into the vector, that is, any one of hosts in which a host-vector system is constructed in a genetic engineering. For example, *E. coli*, which is the most widely known, can be used. In this case, when a vector using an inducible promoter is used, an inducer may be used for expression of the fusion protein.

Step (c): Recovery of Fusion Protein

The present step is to recover the fusion protein by binding the above-produced fusion protein to a column to which the tag for purification, which is fused in the fusion protein, binds.

The above-produced fusion protein may be present in the host or discharged outside the host. Any case requires a process for separating the fusion protein from the intracellular/extracellular protein or other substances.

In the present step, the tag for purification fused to the fusion protein can be used for separation and purification. Only the desired fusion protein is bound using a column (resin) to which the tag for purification binds, and the remaining substances are eluted to lead separation and purification.

Meanwhile, in the present step, the fusion protein may be recovered by unfolding the produced fusion protein, and then refolding it by binding to the column. In addition, the present step may unfold the produced fusion protein, refold it, and then bind it to the column to recover the fusion protein.

When the produced fusion protein is expressed as an inclusion body, it is difficult to expect biological activity in this form. Thus, a process is required to return to its original form, which includes unfolding and refolding processes. Unfolding and refolding processes can be performed using known techniques, so detailed description thereof will be omitted.

Step (d): Recovering TLR5 Agonist Protein

The present step is to recover the TLR5 agonist protein by treating the above-recovered fusion protein with the ubiquitin cleavage enzyme to cleave the site to which the ubiquitin binds.

In order to minimize the possibility of inducing the immune response and inhibiting binding with TLR5, the fusion partner binding to the fusion protein should be removed. In the present step, the fusion partner is removed using the ubiquitin cleavage enzyme.

In the present step, the treatment with the ubiquitin cleavage enzyme can be performed, for example, in the state where the fusion protein is bound to the column, and the fusion protein can also be treated after elution from the column.

In the present step, the ubiquitin cleavage enzyme may be various ones, for example, USP and UCH.

Advantageous Effects

According to the present disclosure, the TLR5 agonist protein can be biologically produced and then easily separated and purified. In particular, the possibility of inhibiting binding to TLR5 and inducing the immune response by the fusion partner can be minimized by effectively removing the fusion partner used for separation and purification.

DESCRIPTION OF DRAWINGS

FIG. 1 is a schematic diagram illustrating a gene sequence of K6UbKMRC011.
FIG. 2 is a base sequence of the K6UbKMRC011 gene.
FIG. 3 is an amino acid sequence of K6UbKMRC011.
FIG. 4 is a schematic diagram illustrating pAP-K6UbKMRC011 plasmid.

BEST MODE

Figure 5:
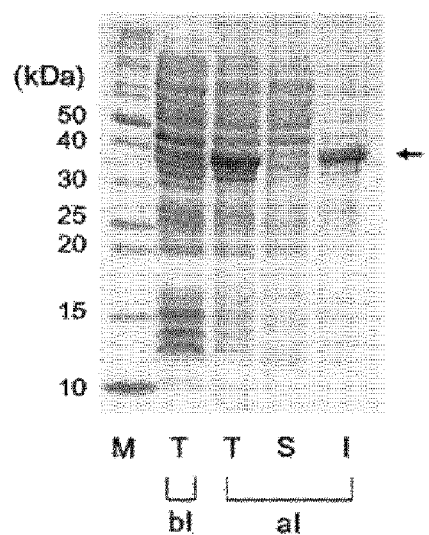
FIG. 5 shows analysis results of the expression levels and solubility of K6UbKMRC011 expressed in *E. coli*.

Hereinafter, the present disclosure will be described in more detail with reference to the following Examples and Experimental examples. However, the scope of the present disclosure is not limited to the following Examples, and includes modifications of equivalent technical ideas.

Example 1: Preparation of K6UbKMRC011-Expressing *E. coli*

(1) Gene Synthesis of K6UbKMRC011

The polypeptide having the amino acid sequence as set forth in SEQ ID NO: 2 (encoded by the nucleic acid sequence as set forth in SEQ ID NO: 1) and the polypeptide having the amino acid sequence as set forth in SEQ ID NO: 4 (encoded by the nucleic acid sequence as set forth in SEQ ID NO: 3) are bound via the polypeptide (linker) having the amino acid sequence as set forth in SEQ ID NO: 6 (encoded by SEQ ID NO: 5), and then are folded to form the D0 domain and D1 domain capable of binding to TLR5.

In the present Example, the fusion gene, "K6UbKMRC011", is synthesized by binding the gene encoding the lysine tag (K6) formed by six consecutive bonds of lysines and the gene encoding the ubiquitin (Ub) to so-called 'TLR5 agonist protein (KMRC011) encoding gene' in which the nucleic acid sequence as set forth in SEQ ID NO: 1 and the nucleic acid sequence as set forth in SEQ ID NO: 3 are combined with mediation by a nucleic acid sequence (linker) as set forth in SEQ ID NO: 5. K6Ub portion and KMRC011 portion were separately amplified using a primary polymerase chain reaction, and the K6Ub portion and the KMRC011 portion were connected through a secondary polymerase chain reaction to synthesize the entire gene of K6UbKMRC011 (See FIG. 1).

The K6Ub portion was amplified using the primers of K6Ub-NdeI-F and KMRC011-R2 and plasmid pUC18-K6Ub containing K6Ub gene as a template. The KMRC011 portion was amplified using primers KMRC011-F2 and KMRC011-BamHI-R2 and the plasmid pUC57-KMRC011 containing the genes of SEQ ID NO: 1, SEQ ID NO: 3, and SEQ ID NO: 5 as a template (See Table 1 below).

TABLE 1

Base sequence of primer used in polymerase chain reaction for K6UbKMRC011 gene synthesis

| No. | Primer's name | Primer sequence |
| --- | --- | --- |
| 1 | K6Ub-NdeI-F | Aatcatatgaagaaaaaaaagaaaaagca gattttcgtcaagact (SEQ ID NO: 10) |
| 2 | KMRC011-R2 | Tgttgataacctgcgccatgccacctctt agccttagc (SEQ ID NO: 11) |
| 3 | KMRC011-F2 | Gctaaggctaagaggtggcgcgcaggtta tcaaca (SEQ ID NO: 12) |
| 4 | KMRC011-BamHI-R2 | Attggatccttagcgcagcaggctcag (SEQ ID NO: 13) |

The entire gene of K6UbKMRC011 was synthesized by overlap-extension PCR using the primers K6Ub-NdeI-F and KMRC011-BamHI-R and K6Ub and KMRC011, products of the first polymerase chain reaction, as a template. The nucleotide sequence of the synthesized K6UbKMRC011 gene and the amino acid sequence deduced from the nucleotide sequence are shown in FIG. 2 (SEQ ID NO: 7) and FIG. 3 (SEQ ID NO: 8), respectively.

(2) Production of K6UbKMRC011 Expression Plasmid

The amplified K6UbKMRC011 gene whose expression was regulated by IPTG was inserted into the NdeI and BamHI restriction enzyme sites of the pAP (owned by AP Technology) expression plasmid containing the tac promoter, thereby constructing the pAP-K6UbKMRC011 plasmid (See FIG. 4).

(3) Production of *Escherichia coli* Expressing K6UbKMRC011

*Escherichia coli* TG1/pAP-K6UbKMRC011 expressing K6UbKMRC011 was finally produced by transforming the pAP-K6UbKMRC011 plasmid into *Escherichia coli* TG1.

Example 2: Production of K6UbKMRC011 Using the Recombinant *Escherichia coli* Produced in Example 1

The production ability of K6UbKMRC011 was confirmed using *Escherichia coli* TG1/pAP-K6UbKMRC011 prepared in the above Example. For the cultivation, medium of yeast extract 5 g/L, tryptone 10 g/L, and sodium chloride 10 g/L was used. The cells were cultured in a 500 mL baffled flask at 37° C. and 200 rpm until the absorbance at 600 nm reached 0.5-1.0, then IPTG was added to 1 mM so that the expression of K6UbKMRC011 was induced, and then cultured for 4 hours.

The K6UbKMRC011-expressing *Escherichia coli*, which had been calibrated in 15 at an absorbance of 600 nm, was disrupted using an ultrasonicator, followed by dividing into soluble and non-soluble fractions under conditions of centrifugation at 12,000 rpm for 20 minutes, and followed by confirming the expression level and the availability of K6UbKMRC011 through SDS-PAGE (sodium dodecyl sulfate polyacrylamide gel electrophoresis) analysis.

The intracellular expression level of the expressed K6UbKMRC011 was confirmed to be about 21% through a densitometer analysis (See FIG. 5). K6UbKMRC011 was observed in mostly the insoluble fraction, and thus K6UbKMRC011 expressed in *Escherichia coli* was confirmed to be an insoluble inclusion body.

Example 3: Method of Refolding Solid Phase of K6UbKMRC011 Produced in Example 2

Figure 6:
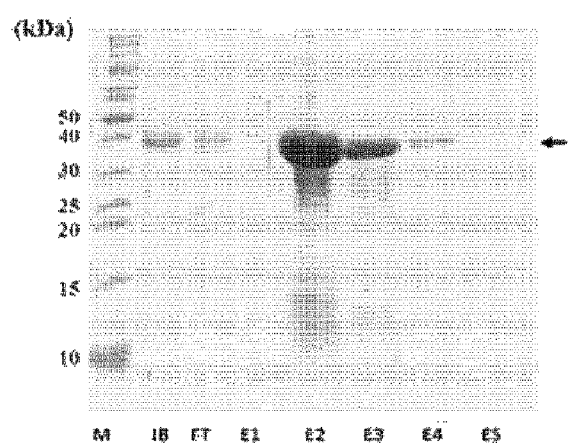
FIG. 6 shows analysis results of SDS-PAGE of solid phase refolded K6UbKMRC011.

Since K6UbKMRC011 expressed in *Escherichia coli* was expressed as an insoluble inclusion body, solid-phase refolding was performed to recover biological activity. *Escherichia coli*, which was disrupted with an ultrasonicator, was centrifuged (12,000 rpm, 20 minutes), and the inclusion body of the resulting K6UbKMRC011 were solubilized with buffer A (pH 7.0, 50 mM sodium phosphate, 8 M urea). Then it was injected to the column filled with a cation exchange resin (SP Sepharose FF, GE Healthcare) equilibrated with Buffer A, and thus the solubilized K6UbKMRC011 bind to the cation exchange resin by electrostatic attraction. Buffer B (pH 7.0, 50 mM sodium phosphate) was injected into the above-mentioned column to remove the urea, and thus K6UbKMRC011 binding to the cation exchange resin was induced to be re-folded. Buffer C (pH 7.0, 50 mM sodium phosphate, 1 M NaCl) was injected into the above-mentioned column to allow the refolded K6UbKMRC011 to be eluted from the cation exchange resin, and each fraction was analyzed by SDS-PAGE (See FIG. 6).

The eluted refolded K6UbKMRC011 was confirmed to have a soluble form. In order to confirm whether it is cleaved by USP1 (ubiquitin-specific protease 1), USP1 was added to the eluted refolded K6UbKMRC011 to a concentration of 10 mg/L and then was reacted at 37° C. for 12 hours.

Figure 7:
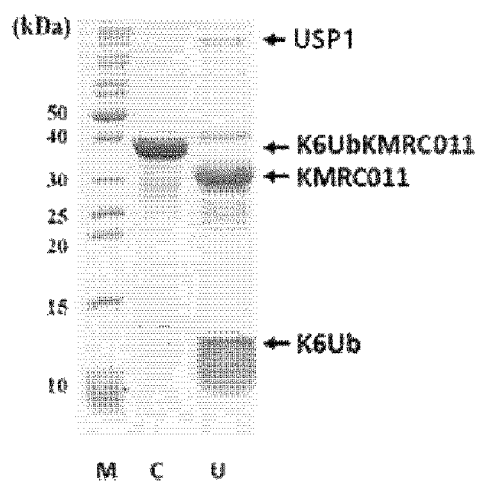
FIG. 7 shows analysis results of cleavage by USP1 of solid phase refolded K6UbKMRC011.

As a result of SDS-PAGE analysis, it was confirmed that most of the refolded K6UbKMRC011 was cleaved by USP1 and separated into K6Ub and KMRC011 (See FIG. 7). At this time, it was also confirmed that USP1 treatment did not decompose the internal structure of the KMRC011 protein.

In addition, the N-terminal sequence of the separated KMRC011 protein was confirmed through "N-terminal sequencing". As a result, it was confirmed that the K6Ub was separated to be departed while the N-terminal amino acid sequence 'A-Q-V—I-N' of the KMRC011 protein was maintained intact.

From the above results, it was confirmed that the KMRC011 protein of the present disclosure was not degraded by treatment with USP1, a ubiquitin cleavage enzyme, and that K6Ub was separated while maintaining the N-terminal thereof intact.

When the fusion partner is removed from the target protein, the enzyme used for the removal should not affect the structure of the target protein. The ubiquitin cleavage enzyme of the present disclosure has no influence on the structure of the target protein, KMRC011.

Figure 8:
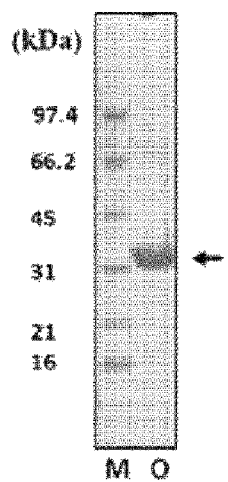
FIG. 8 shows results of the isolation and purification of the TLR5 agonist protein through on-column cleavage.

Example 4: Method for Separating and Purifying KMRC011 from Solid-Phase Refolded K6UbKMRC011 in Example 3—on Column Cleavage The USP1 solution (10 mg/L) was purposely circulated to separate and purify only KMRC011 while the solid-phase refolded K6UbKMRC011 electrostatically bound to the cation exchange resin without elution thereof (See FIG. 8).

The separated and purified KMRC011 was identified as AQVINTNSLS in the amino terminal sequence analysis. Thus, it was confirmed that the USP1 clearly cleaved the immediate side of K6Ub of K6UbKMRC011 so that only KMRC011 was separated and purified.

Example 5: Analysis Results of Cleavage of K6UbKMRC011 by Application of Various Ubiquitin Cleavage Enzymes In the present embodiment, various kinds of ubiquitin cleavage enzymes other than USP1 described in Example 3 were applied to K6UbKMRC011 to confirm whether the target protein KMRC011 was completely separated from K6Ub.

The various ubiquitin cleavage enzymes shown in Table 2 below were added to the refolded K6UbKMRC011 in soluble form obtained in Example 3, so as to have a concentration of 10 mg/L and reacted at 37° C. for 12 hours.

TABLE 2

| Name of Product | Manufacturer | Catalog No. | Lot No. | Generic name of Enzyme |
| --- | --- | --- | --- | --- |
| UBP | AP Technology Corp. | — | P3S021-04 | USP1 |
| Recombinant Human USP2 Catalytic Domain | Boston Biochem, Inc. | E-504 | 09341414A | USP2 |
| Recombinant Human His6 USP10 | Boston Biochem, Inc. | E-592 | 28570115A | USP10 |
| UCH-L3, human recombinant | Boston Biochem, Inc. | E-325 | 34709013 | UCH-L3 |
| Recombinant Human UCH-L5/ UCH37 | Boston Biochem, Inc. | E-327 | 25967314A | UCH-L5/ UCH37 |

Figure 9:
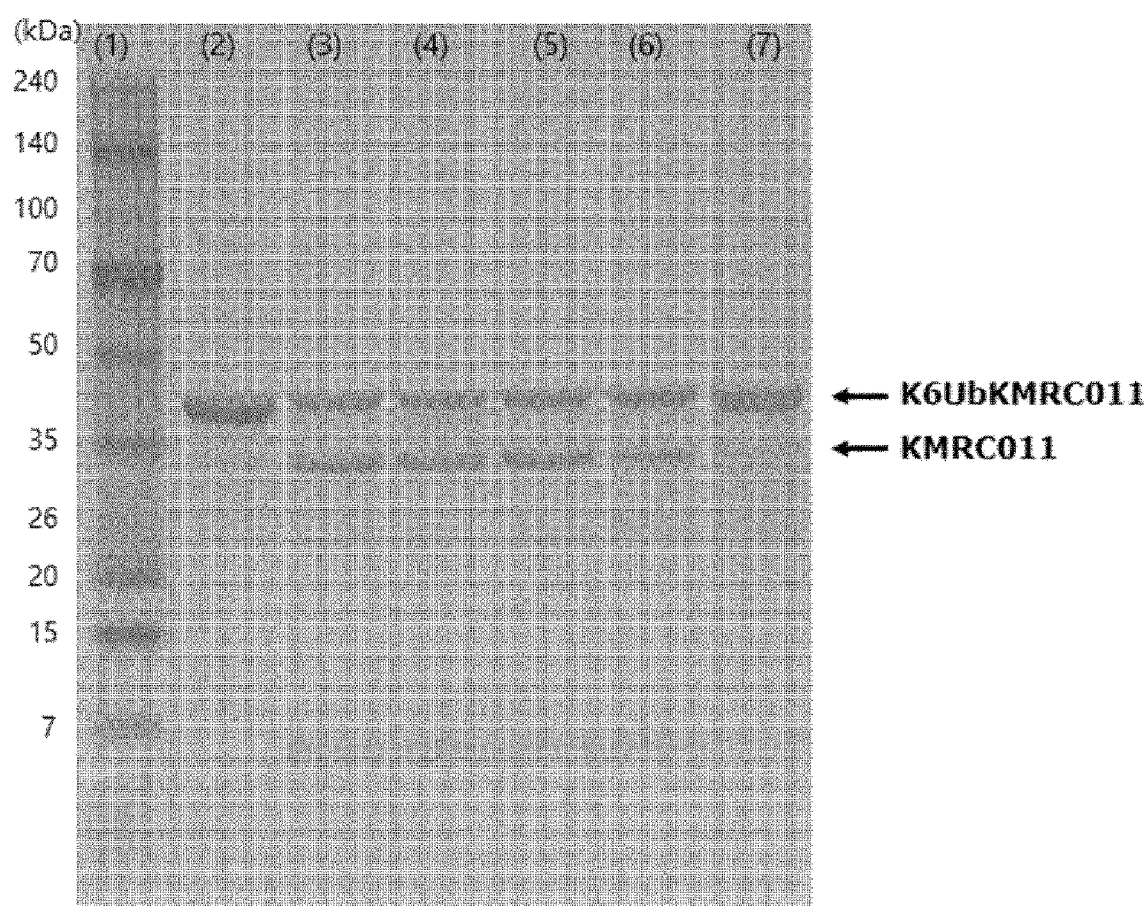
FIG. 9 shows analysis results of cleavage of K6UbKMRC011 according to application of various ubiquitin cleavage enzymes.

The experimental results are illustrated in FIG. 9. FIG. 9 shows analysis results of cleavage of K6UbKMRC011 by application of various ubiquitin cleavage enzymes. In FIG. 9, lane 1 indicates Protein Mw size marker, lane 2 indicates K6UbKMRC011, lane 3 indicates K6UbKMRC011+USP1, lane 4 indicates K6UbKMRC011+USP2, lane 5 indicates K6UbKMRC011+USP10, lane 6 indicates K6UbKMRC011+UCH-L3, and lane 7 indicates K6UbKMRC011+UCH-L5/UCH37.

As shown in FIG. 9, which is the result of SDS-PAGE analysis, it was confirmed that the refolded K6UbKMRC011 was cleaved by the ubiquitin cleavage enzymes shown in Table 2 and correctly separated into K6Ub and KMRC011. At this time, it was also confirmed that the internal structure of the KMRC011 protein was not degraded by the treatment of these enzymes.

Further, as a result of confirming the N-terminal sequence of the separated KMRC011 protein through 'N-terminal sequencing', K6Ub was separated while the N-terminal amino acid sequence 'A-Q-V—I-N' of the KMRC011 protein was maintained intact as in Example 3.

As described above, it was confirmed that all of the ubiquitin cleavage enzymes used in the present experiments correctly cleaved the immediate side of K6Ub of K6UbKMRC011. Therefore, it was confirmed that USP1-based and UCH-based ubiquitin cleavage enzymes as well as USP1 of Example 3 can cleave the immediate side of K6Ub of K6UbKMRC011 so as to separate KMRC011 without damage of KMRC011.

Further, from the above-described various experimental results, it can be concluded that all types of the ubiquitin cleavage enzymes can precisely cleave the immediate side of K6Ub of K6UbKMRC011 so as to separate KMRC011 without damage of KMRC011.

The invention claimed is:

1. A method of producing a Toll-like receptor-5 (TLR5) agonist protein, comprising the steps of:
   (a) producing a vector that comprises (i) a fusion nucleic acid that encodes the TLR5 agonist protein that comprises the amino acid sequence of SEQ ID NO: 2 and the amino acid sequence of SEQ ID NO: 4; (ii) a nucleic acid that encodes ubiquitin, and (iii) a nucleic acid that encodes a tag for purification;
   (b) producing a fusion protein by transforming a host with the vector in step (a) and then expressing the fusion nucleic acid;
   (c) recovering the fusion protein by binding the fusion protein of step (b) to a column that the tag for purification binds; and
   (d) recovering the TLR5 agonist protein by treating the recovered fusion protein of step (c) with a ubiquitin cleavage enzyme to cleave the site to which the ubiquitin binds,
   wherein the ubiquitin cleavage enzyme is ubiquitin-specific protease (USP) or ubiquitin C-terminal hydrolase (UCH),
   wherein the fusion nucleic acid has a nucleotide sequence as set forth in SEQ ID NO: 7.

2. The method of claim 1, wherein the TLR5 agonist protein comprises a polypeptide having the amino acid sequence as set forth in SEQ ID NO: 2 and the polypeptide having the amino acid sequence as set forth in SEQ ID NO: 4 that are bound via a linker as set forth in SEQ ID NO: 6.

3. The method of claim 1, wherein the nucleic acid encoding the ubiquitin is linked to the 5' terminal of the nucleic acid encoding the TLR5 agonist protein and the nucleic acid encoding the tag for purification is linked to the 5' terminal of the nucleic acid encoding the ubiquitin.

4. The method of claim 1, wherein the host is *Escherichia coli*.

5. The method of claim 1, wherein the treatment of the ubiquitin cleavage enzyme of step (d) is performed in the state that the fusion protein binds to the column.

6. The method of claim 1, wherein the treatment of the ubiquitin cleavage enzyme of step (d) is performed after the fusion protein is eluted from the column.

7. The method of claim 1, wherein the ubiquitin comprises an amino acid sequence cleaved by the ubiquitin cleavage enzyme.

8. The method of claim 1, wherein the tag for purification is a histidine tag (His-tag) or a lysine tag formed by six consecutive bindings of lysines.

9. The method of claim 1, wherein in the step (c), the fusion protein is recovered by unfolding the produced fusion protein, then binding the fusion protein to the column, and then refolding the fusion protein.

10. The method of claim 1, wherein in the step (c), the fusion protein is recovered by unfolding the produced fusion protein, then refolding the fusion protein, and then binding the fusion protein to the column.

* * * * *

SEQUENCE LISTING

<160> NUMBER OF SEQ ID NOS: 13

<210> SEQ ID NO 1
<211> LENGTH: 525
<212> TYPE: DNA
<213> ORGANISM: Salmonella enterica

<400> SEQUENCE: 1

```
gcgcaggtta tcaacaccaa ctctctgtcc ctgctgaccc aaaacaatct gaacaaatcc      60
cagagctccc tgagctccgc gatcgagcgt ctgtcctccg gcctgcgtat taatagcgcc     120
aaagacgatg ccgcgggtca ggcgatcgct aaccgcttca cttccaacat taaaggcctg     180
actcaggcct cccgtaacgc aaacgacggt attagcatcg ctcagactac tgaaggtgct     240
ctgaacgaaa ttaacaacaa cctgcagcgc gtccgtgaac tgagcgtcca ggcaaccaac     300
ggtactaact ctgacagcga tctgaaatcc attcaggatg aaattcagca gcgtctggaa     360
gaaatcgacc gcgtgtctaa ccagacgcaa ttcaacggcg taaaggtgct gtctcaggac     420
aatcagatga aaatccaagt tggtgcgaac gacggcgaga ctatcaccat cgatctgcag     480
aaaatcgacg ttaaatccct gggtctggac ggttttaacg taaac                    525
```

<210> SEQ ID NO 2
<211> LENGTH: 175
<212> TYPE: PRT
<213> ORGANISM: Salmonella enterica

<400> SEQUENCE: 2

```
Ala Gln Val Ile Asn Thr Asn Ser Leu Ser Leu Leu Thr Gln Asn Asn
1               5                   10                  15

Leu Asn Lys Ser Gln Ser Ser Leu Ser Ser Ala Ile Glu Arg Leu Ser
            20                  25                  30

Ser Gly Leu Arg Ile Asn Ser Ala Lys Asp Asp Ala Ala Gly Gln Ala
        35                  40                  45

Ile Ala Asn Arg Phe Thr Ser Asn Ile Lys Gly Leu Thr Gln Ala Ser
    50                  55                  60

Arg Asn Ala Asn Asp Gly Ile Ser Ile Ala Gln Thr Thr Glu Gly Ala
65                  70                  75                  80

Leu Asn Glu Ile Asn Asn Asn Leu Gln Arg Val Arg Glu Leu Ser Val
                85                  90                  95

Gln Ala Thr Asn Gly Thr Asn Ser Asp Ser Asp Leu Lys Ser Ile Gln
            100                 105                 110

Asp Glu Ile Gln Gln Arg Leu Glu Glu Ile Asp Arg Val Ser Asn Gln
        115                 120                 125

Thr Gln Phe Asn Gly Val Lys Val Leu Ser Gln Asp Asn Gln Met Lys
    130                 135                 140

Ile Gln Val Gly Ala Asn Asp Gly Glu Thr Ile Thr Ile Asp Leu Gln
145                 150                 155                 160

Lys Ile Asp Val Lys Ser Leu Gly Leu Asp Gly Phe Asn Val Asn
                165                 170                 175
```

<210> SEQ ID NO 3
<211> LENGTH: 315
<212> TYPE: DNA

<213> ORGANISM: Salmonella enterica

<400> SEQUENCE: 3

```
accctgatca acgaggatgc agcggcggct aagaaatcta ctgccaaccc tctggccagc    60
atcgacagcg ctctgagcaa agttgatgcg gtgcgttctt ctctgggcgc aatccagaat   120
cgcttcgatt ccgctatcac gaatctgggc aacaccgtta ccaacctgaa ctctgctcgt   180
agccgtatcg aagacgcaga ttatgcgacc gaagtatcta acatgtctaa agcacagatt   240
ctgcagcagg ctggtacctc tgttctggct caggcaaacc aggtgccgca aaacgttctg   300
tctctgctgc gctaa                                                    315
```

<210> SEQ ID NO 4
<211> LENGTH: 104
<212> TYPE: PRT
<213> ORGANISM: Salmonella enterica

<400> SEQUENCE: 4

```
Thr Leu Ile Asn Glu Asp Ala Ala Ala Lys Lys Ser Thr Ala Asn
1               5                   10                  15

Pro Leu Ala Ser Ile Asp Ser Ala Leu Ser Lys Val Asp Ala Val Arg
            20                  25                  30

Ser Ser Leu Gly Ala Ile Gln Asn Arg Phe Asp Ser Ala Ile Thr Asn
        35                  40                  45

Leu Gly Asn Thr Val Thr Asn Leu Asn Ser Ala Arg Ser Arg Ile Glu
    50                  55                  60

Asp Ala Asp Tyr Ala Thr Glu Val Ser Asn Met Ser Lys Ala Gln Ile
65                  70                  75                  80

Leu Gln Gln Ala Gly Thr Ser Val Leu Ala Gln Ala Asn Gln Val Pro
                85                  90                  95

Gln Asn Val Leu Ser Leu Leu Arg
            100
```

<210> SEQ ID NO 5
<211> LENGTH: 48
<212> TYPE: DNA
<213> ORGANISM: Artificial Sequence
<220> FEATURE:
<223> OTHER INFORMATION: Linker

<400> SEQUENCE: 5

```
tctccaggta tctctggtgg cggtggtggc attctggact ccatgggt              48
```

<210> SEQ ID NO 6
<211> LENGTH: 16
<212> TYPE: PRT
<213> ORGANISM: Artificial Sequence
<220> FEATURE:
<223> OTHER INFORMATION: Linker

<400> SEQUENCE: 6

```
Ser Pro Gly Ile Ser Gly Gly Gly Gly Ile Leu Asp Ser Met Gly
1               5                   10                  15
```

<210> SEQ ID NO 7
<211> LENGTH: 1134
<212> TYPE: DNA
<213> ORGANISM: Artificial Sequence
<220> FEATURE:
<223> OTHER INFORMATION: K6UbKMRC011

<400> SEQUENCE: 7

-continued

```
atgaagaaaa aaaagaaaaa gcagattttc gtcaagactt tgaccggtaa aaccataaca      60
ttggaagttg aatcttccga taccatcgac aacgttaagt cgaaaattca agacaaggaa     120
ggtatccctc cagatcaaca aagattgatc tttgccggta agcagctaga agacggtaga     180
acgctgtctg attacaacat tcagaaggag tccaccttac atcttgtgct aaggctaaga     240
ggtggcgcgc aggttatcaa caccaactct ctgtccctgc tgacccaaaa caatctgaac     300
aaatcccaga gctccctgag ctccgcgatc gagcgtctgt cctccggcct gcgtattaat     360
agcgccaaag acgatgccgc gggtcaggcg atcgctaacc gcttcacttc caacattaaa     420
ggcctgactc aggcctcccg taacgcaaac gacggtatta gcatcgctca gactactgaa     480
ggtgctctga acgaaattaa caacaacctg cagcgcgtcc gtgaactgag cgtccaggca     540
accaacggta ctaactctga cagcgatctg aaatccattc aggatgaaat tcagcagcgt     600
ctggaagaaa tcgaccgcgt gtctaaccag acgcaattca acggcgtaaa ggtgctgtct     660
caggacaatc agatgaaaat ccaagttggt gcgaacgacg gcgagactat caccatcgat     720
ctgcagaaaa tcgacgttaa atccctgggt ctggacggtt ttaacgtaaa ctctccaggt     780
atctctggtg gcggtggtgg cattctggac tccatgggta ccctgatcaa cgaggatgca     840
gcggcggcta agaaatctac tgccaaccct ctggccagca tcgacagcgc tctgagcaaa     900
gttgatgcgg tgcgttcttc tctgggcgca atccagaatc gcttcgattc cgctatcacg     960
aatctgggca caccgttaca acctgaac tctgctcgta gccgtatcga agacgcagat    1020
tatgcgaccg aagtatctaa catgtctaaa gcacagattc tgcagcaggc tggtacctct    1080
gttctggctc aggcaaacca ggtgccgcaa acgttctgt ctctgctgcg ctaa           1134
```

<210> SEQ ID NO 8
<211> LENGTH: 377
<212> TYPE: PRT
<213> ORGANISM: Artificial Sequence
<220> FEATURE:
<223> OTHER INFORMATION: K6UbKMRC011

<400> SEQUENCE: 8

```
Met Lys Lys Lys Lys Lys Gln Ile Phe Val Lys Thr Leu Thr Gly
1               5                   10                  15
Lys Thr Ile Thr Leu Glu Val Glu Ser Ser Asp Thr Ile Asp Asn Val
            20                  25                  30
Lys Ser Lys Ile Gln Asp Lys Glu Gly Ile Pro Pro Asp Gln Gln Arg
        35                  40                  45
Leu Ile Phe Ala Gly Lys Gln Leu Glu Asp Gly Arg Thr Leu Ser Asp
    50                  55                  60
Tyr Asn Ile Gln Lys Glu Ser Thr Leu His Leu Val Leu Arg Leu Arg
65                  70                  75                  80
Gly Gly Ala Gln Val Ile Asn Thr Asn Ser Leu Ser Leu Leu Thr Gln
                85                  90                  95
Asn Asn Leu Asn Lys Ser Gln Ser Ser Leu Ser Ser Ala Ile Glu Arg
            100                 105                 110
Leu Ser Ser Gly Leu Arg Ile Asn Ser Ala Lys Asp Asp Ala Ala Gly
        115                 120                 125
Gln Ala Ile Ala Asn Arg Phe Thr Ser Asn Ile Lys Gly Leu Thr Gln
    130                 135                 140
Ala Ser Arg Asn Ala Asn Asp Gly Ile Ser Ile Ala Gln Thr Thr Glu
145                 150                 155                 160
```

-continued

```
Gly Ala Leu Asn Glu Ile Asn Asn Asn Leu Gln Arg Val Arg Glu Leu
            165                 170                 175
Ser Val Gln Ala Thr Asn Gly Thr Asn Ser Asp Ser Asp Leu Lys Ser
        180                 185                 190
Ile Gln Asp Glu Ile Gln Gln Arg Leu Glu Glu Ile Asp Arg Val Ser
        195                 200                 205
Asn Gln Thr Gln Phe Asn Gly Val Lys Val Leu Ser Gln Asp Asn Gln
    210                 215                 220
Met Lys Ile Gln Val Gly Ala Asn Asp Gly Glu Thr Ile Thr Ile Asp
225                 230                 235                 240
Leu Gln Lys Ile Asp Val Lys Ser Leu Gly Leu Asp Gly Phe Asn Val
            245                 250                 255
Asn Ser Pro Gly Ile Ser Gly Gly Gly Gly Ile Leu Asp Ser Met
        260                 265                 270
Gly Thr Leu Ile Asn Glu Asp Ala Ala Ala Lys Lys Ser Thr Ala
        275                 280                 285
Asn Pro Leu Ala Ser Ile Asp Ser Ala Leu Ser Lys Val Asp Ala Val
    290                 295                 300
Arg Ser Ser Leu Gly Ala Ile Gln Asn Arg Phe Asp Ser Ala Ile Thr
305                 310                 315                 320
Asn Leu Gly Asn Thr Val Thr Asn Leu Asn Ser Ala Arg Ser Arg Ile
            325                 330                 335
Glu Asp Ala Asp Tyr Ala Thr Glu Val Ser Asn Met Ser Lys Ala Gln
        340                 345                 350
Ile Leu Gln Gln Ala Gly Thr Ser Val Leu Ala Gln Ala Asn Gln Val
        355                 360                 365
Pro Gln Asn Val Leu Ser Leu Leu Arg
    370                 375

<210> SEQ ID NO 9
<211> LENGTH: 34
<212> TYPE: PRT
<213> ORGANISM: Artificial Sequence
<220> FEATURE:
<223> OTHER INFORMATION: Synthetic peptide

<400> SEQUENCE: 9

Met Arg Gly Ser His His His His His His Gly Met Ala Ser Met Thr
1               5                   10                  15
Gly Gly Gln Gln Met Gly Arg Asp Leu Tyr Asp Asp Asp Lys Asp
            20                  25                  30
Pro Met

<210> SEQ ID NO 10
<211> LENGTH: 45
<212> TYPE: DNA
<213> ORGANISM: Artificial Sequence
<220> FEATURE:
<223> OTHER INFORMATION: Primer (K6Ub-NdeI-F)

<400> SEQUENCE: 10
aatcatatga agaaaaaaaa gaaaaagcag attttcgtca agact          45

<210> SEQ ID NO 11
<211> LENGTH: 38
<212> TYPE: DNA
<213> ORGANISM: Artificial Sequence
<220> FEATURE:
<223> OTHER INFORMATION: Primer (KMRC011-R2)
```

```
<400> SEQUENCE: 11
tgttgataac ctgcgccatg ccacctctta gccttagc                               38

<210> SEQ ID NO 12
<211> LENGTH: 35
<212> TYPE: DNA
<213> ORGANISM: Artificial Sequence
<220> FEATURE:
<223> OTHER INFORMATION: Primer (KMRC011-F2)

<400> SEQUENCE: 12
gctaaggcta agaggtggcg cgcaggttat caaca                                  35

<210> SEQ ID NO 13
<211> LENGTH: 27
<212> TYPE: DNA
<213> ORGANISM: Artificial Sequence
<220> FEATURE:
<223> OTHER INFORMATION: Primer (KMRC011-BamHI-R2)

<400> SEQUENCE: 13
attggatcct tagcgcagca ggctcag                                           27
```